United States Patent
Holm et al.

(10) Patent No.: US 7,858,838 B2
(45) Date of Patent: Dec. 28, 2010

(54) CONFORMABLE WOUND DRESSING

(75) Inventors: David R. Holm, Hudson, WI (US); Richard L. Jacobson, Oakdale, MN (US); Donald H. Lucast, North St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 623 days.

(21) Appl. No.: 11/463,853

(22) Filed: Aug. 10, 2006

(65) Prior Publication Data

US 2008/0039759 A1 Feb. 14, 2008

(51) Int. Cl.
*A61F 13/00* (2006.01)

(52) U.S. Cl. .............. 602/58; 602/42; 602/43; 602/54; 602/57

(58) Field of Classification Search ............. 602/41–59; 604/304–308; 128/888, 889; D24/189
See application file for complete search history.

(56) References Cited

U.S. PATENT DOCUMENTS

| | | | | |
|---|---|---|---|---|
| 2,148,882 | A | 2/1939 | Scholl | 128/153 |
| RE24,906 | E | 12/1960 | Ulrich | 206/59 |
| 3,389,827 | A | 6/1968 | Abere et al. | 220/53 |
| 3,529,597 | A | 9/1970 | Fuzak | 128/157 |
| 3,971,374 | A | 7/1976 | Wagner | 128/155 |
| 4,112,213 | A | 9/1978 | Waldman | 526/279 |
| 4,310,509 | A | 1/1982 | Berglund et al. | 424/28 |
| 4,323,557 | A | 4/1982 | Rosso et al. | 424/28 |
| 4,472,480 | A | 9/1984 | Olson | 428/332 |
| 4,614,183 | A | 9/1986 | McCracken et al. | 128/132 |
| 4,619,253 | A | 10/1986 | Anhauser et al. | 218/156 |
| 4,737,410 | A | 4/1988 | Kantner | 428/343 |
| 4,738,257 | A | 4/1988 | Meyer et al. | 128/156 |
| 5,088,483 | A | 2/1992 | Heinecke | 602/46 |
| 5,160,315 | A | 11/1992 | Heinecke et al. | 602/57 |
| 5,429,592 | A | 7/1995 | Jensen | 602/59 |
| 5,505,958 | A | 4/1996 | Bello et al. | 424/449 |
| 5,531,855 | A | 7/1996 | Heinecke et al. | 156/252 |
| 5,622,711 | A | 4/1997 | Chen | 424/445 |
| 5,633,010 | A | 5/1997 | Chen | 424/448 |
| 5,656,167 | A | 8/1997 | Martz | |
| 5,683,354 | A | 11/1997 | Levy | 602/54 |
| 5,704,905 | A | 1/1998 | Jensen et al. | 602/58 |
| 5,738,642 | A | 4/1998 | Heinecke et al. | 602/58 |

(Continued)

FOREIGN PATENT DOCUMENTS

EP 0 303 422 A2 2/1989

(Continued)

OTHER PUBLICATIONS

3M Tegasorb™ THIN and 3M Tegasorb Hydrocolloid Dressings; Application and Removal Techniques brochure;3M Health Care Division.

(Continued)

*Primary Examiner*—Kim M Lewis
(74) *Attorney, Agent, or Firm*—Trisha D. Adamson (57) ABSTRACT

A wound dressing comprising a dressing support layer configured to retain and deliver the wound dressing to a wound, the dressing support layer having a radial configuration that forms a plurality of alternating covered and uncovered portions of the backing layer along the perimeter of the wound dressing.

23 Claims, 3 Drawing Sheets

U.S. PATENT DOCUMENTS

| | | | |
|---|---|---|---|
| 5,773,022 A | 6/1998 | Nyqvist-Mayer et al. | 424/443 |
| 5,820,578 A | 10/1998 | Johansen | 602/57 |
| 5,827,213 A | 10/1998 | Jensen | 602/62 |
| D408,541 S | 4/1999 | Dunshee et al. | D24/189 |
| 5,902,260 A | 5/1999 | Gilman et al. | 602/57 |
| 5,928,972 A * | 7/1999 | Mashiko et al. | 442/334 |
| 5,998,694 A | 12/1999 | Jensen et al. | 602/57 |
| 6,074,965 A | 6/2000 | Bodenschatz | |
| 6,169,224 B1 | 1/2001 | Heinecke et al. | 602/58 |
| 6,264,976 B1 | 7/2001 | Heinecke et al. | 424/443 |
| 6,362,387 B1 * | 3/2002 | Carlson et al. | 602/41 |
| D480,144 S | 9/2003 | Adams et al. | D24/189 |
| D484,601 S | 12/2003 | Griffiths et al. | D24/189 |
| D493,230 S | 7/2004 | Liedtke et al. | D24/189 |
| 6,838,589 B2 | 1/2005 | Liedtke et al. | 602/58 |
| D503,982 S | 4/2005 | Liedtke et al. | D24/189 |
| 6,927,315 B1 | 8/2005 | Heinecke et al. | |
| 7,030,288 B2 | 4/2006 | Liedtke et al. | |
| 2003/0088202 A1 | 5/2003 | Gilman | 602/46 |
| 2004/0049146 A1 | 3/2004 | Kolte et al. | 602/61 |
| 2005/0113733 A1 * | 5/2005 | Liedtke et al. | 602/57 |
| 2006/0142687 A1 | 6/2006 | Liedtke et al. | 602/58 |

FOREIGN PATENT DOCUMENTS

| | | |
|---|---|---|
| GB | 1114893 | 5/1968 |
| GB | 1 251 203 | 10/1971 |
| WO | WO 88/08787 | 11/1988 |
| WO | WO 97/07760 A1 | 3/1997 |

OTHER PUBLICATIONS

3M Tegasorb™ Hydrocolloid Dressing 3M Tegasorb™ THIN Hydrocolloid Dressing; Product Profile brochure; 3M Health Care Division.

* cited by examiner

CONFORMABLE WOUND DRESSING

BACKGROUND OF THE INVENTION

Wound dressings using an absorbent central area surrounded by a larger adhesive film are known. For example, U.S. Pat. No. 5,738,642 (the '642 patent) shows a wound dressing and support system comprising a thick absorbent pad placed in the center of a thin backing. A carrier frame surrounds the perimeter of the wound dressing, providing support (e.g. rigidity) to the backing to facilitate handling of the dressing during application to a wound. The dressing taught in the '642 patent is useful for application to a large variety of wounds. However, a need remains for a wound dressing that can be more effectively supported and/or more conformable for application to irregular surfaces, such as a heel or shoulder. Currently, wound dressings are sometimes cut toward their center to make a cone shaped dressing, but these dressings have significant limitations, including the risk of infection along the line of the cut line, difficulty in applying with one hand, and leakage of fluids from the wound along the cut line.

Therefore, a need remains for an improved wound dressing configured for better support to the wound dressing and for application to a rounded or other irregularly shaped body part.

SUMMARY OF THE INVENTION

The present invention provides a wound dressing having a thin, flexible periphery and support system that facilitates handling the wound dressing. The wound dressing is constructed so as to have improved adhesion to irregular shaped surfaces, such as a heel, and to permit easy application to the irregular shaped surfaces. The wound dressing and support system are well suited to positioning an absorbent pad onto a concave or convex surface. For example, the wound dressing and support system are suitable for applying an absorbent pad to the heel of a foot, while maintaining an intact sterile perimeter around the wound dressing.

In certain implementations the wound dressing and support system include a wound dressing comprising an adhesive layer on a backing layer. Optionally, an absorbent pad or material is applied or attached to the adhesive layer. A dressing support layer is applied to the backing layer, and is configured to retain and deliver the wound dressing to a wound. The dressing support layer remains on the wound dressing after application of the wound dressing to the wound. In most embodiments, the dressing support layer has a radial configuration of extensions that support the backing layer along the perimeter of the wound dressing, while also allowing the dressing to be easily applied to convex surfaces and other non-planar surfaces.

In some embodiments, the wound dressing support layer is permanently attached to the bottom of the backing layer either between the backing layer and the adhesive layer or on the adhesive layer. In some embodiments, the dressing support layer is permanently attached to the top of the backing layer.

In one embodiment, a wound dressing and support system is provided that comprises a wound dressing comprising a backing layer with a first and second major surface, and a dressing support layer permanently attached to at least one of the first major surface and second major surface of the backing layer, wherein the dressing support layer has a radial configuration that forms a plurality of alternating covered and uncovered portions of the backing layer along the perimeter of the wound dressing.

In another embodiment, a wound dressing and support system is provided, comprising a wound dressing substrate configured to be placed on a wound, the dressing substrate having an absorbent interior surrounded by a flexible less absorbent periphery; and a dressing support substrate configured to be permanently attached to the wound dressing substrate wherein the support substrate has one or more central portions positioned proximate the interior and a plurality of extensions radiating from the one or more central portions toward the periphery of the dressing substrate.

In another embodiment, a wound dressing and support system is provided, comprising a wound dressing that comprises: an elastic film backing having first and second major surfaces and a periphery; an adhesive on the first major surface of the backing; and an absorbent pad on the first major surface of the backing, wherein the absorbent pad has a size and position along the backing such that the periphery of the backing extends substantially beyond the absorbent pad, wherein the absorbent pad comprises hydrocolloid or hydrogel materials, wherein the absorbent pad is substantially thicker, heavier and stiffer than the elastic film backing. A support system is also provided that is permanently attached to the second major surface of the backing, wherein the support layer comprises a plurality of extensions radiating from one or more central areas toward the outer edge of the periphery of the wound dressing, and wherein the support layer is substantially more rigid than the backing to facilitate handling of the dressing.

In another embodiment, a wound dressing and support system is provided comprising a wound dressing that comprises: an elastic film backing having first and second major surfaces and a periphery; an adhesive on the first major surface of the backing; and a support system comprising an absorbent pad on the first major surface of the backing, wherein the absorbent pad includes hydrocolloid or hydrogel materials, wherein the absorbent pad is substantially thicker, heavier and stiffer than the elastic film backing, and wherein the absorbent pad comprises a plurality of extensions radiating from one or more central areas toward the outer edge of the periphery of the wound dressing.

In another embodiment, a wound dressing and support system is provided comprising a wound dressing that comprises: an elastic film backing having first and second major surfaces and a periphery; an adhesive on the first major surface of the backing; and an absorbent pad on the first major surface of the backing, wherein the absorbent pad is a size and position along the backing such that the periphery of the backing extends substantially beyond the absorbent pad, and wherein the absorbent pad comprises hydrocolloid or hydrogel materials. A support system is also provided that is attached on the first major surface of the backing, wherein the support layer comprises a plurality of extensions radiating from one or more central areas toward the outer edge of the periphery of the wound dressing, and wherein the support layer being substantially more rigid than the backing to facilitate handling of the dressing.

These and various other advantages and features characterizing the invention are pointed out with particularity in the claims annexed hereto and forming a part hereof. However, for a better understanding of the invention, its advantages, and objects obtained by its use, reference should be made to the accompanying drawings and descriptive matter, in which embodiments of the invention are illustrated and described.

BRIEF DESCRIPTION OF THE DRAWINGS

The invention will be further described with reference to the drawings, wherein corresponding reference characters indicate corresponding parts throughout the several views, and wherein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is directed to a wound dressing and support system, and methods of making the wound dressing and support system. The wound dressing and support system are particularly well suited to application over a convex surface of a patient, such as a patient's heel. The wound dressing permits a highly absorbent material to be placed against the wound, while the support system aids in handling the wound dressing and forming a seal around the convex or irregularly shaped area surrounding the wound.

In some implementations the wound dressing comprises an absorbent pad, a backing layer, and an adhesive layer on the backing layer facing the absorbent pad. The adhesive layer and backing layer form a perimeter around the absorbent pad and hold the absorbent pad in place on a wound. The perimeter formed by the adhesive layer and backing layer keeps the absorbent pad properly positioned, and also helps maintain a sterile environment around the wound. The adhesive layer and backing layer are typically extremely thin, and generally very flexible. If the adhesive layer and backing layer are not properly supported during application, the layers can easily fold over and adhere to themselves, preventing proper application over a wound. The support system described herein provides an easy and effective way to apply the wound dressing to a patient while effectively supporting the perimeter of the dressing to prevent excessive undesirable folding, while allowing controlled, limited folding of the backing layer sufficient to properly contact the patient's uneven skin surface.

The wound dressing contains portions of a highly flexible backing layer along the periphery of the dressing, and portions of relatively more rigid dressing support layer along the periphery. These flexible and more rigid portions alternate around the periphery of the dressing. The more rigid portions are formed from a dressing support layer that is permanently attached to the backing layer and that remains on the wound dressing after the dressing is applied. The dressing support layer can be permanently attached to either side of the backing layer, e.g., the dressing support layer can be on the top of the backing layer or the dressing support layer can be on the side of the backing layer facing the absorbent pad when one is used. These more rigid portions of the dressing support layer facilitate handling of the dressing (for example, by preventing fold-over of the flexible portions of the backing onto itself) prior to application. The wound dressing is highly conformable, and is easy and fast to apply to a wound site. There is no need to remove and dispose of the dressing support layer after the dressing is applied to the wound.

In all embodiments, the support layer is permanently attached to the backing layer. As used herein, "permanently attached" means that the dressing support layer cannot be removed from the backing layer without significantly damaging or destroying the backing layer, thereby rendering the wound dressing nonfunctional. The dressing support layer can be permanently attached to the backing layer or permanently attached by an attachment layer, such as an adhesive.

Because the dressing support layer is permanently attached to the backing layer, there is no upward force applied to the edge of the backing layer once the wound dressing is in place. This lack of force contrasts with peel forces of conventional support layers, which are generally removed from the backing layer and can lift portions of the backing layer, particularly the perimeter, off the surface of the patient, potentially loosening the dressing or creating a path for leakage of fluids from the wound.

Figure 1:
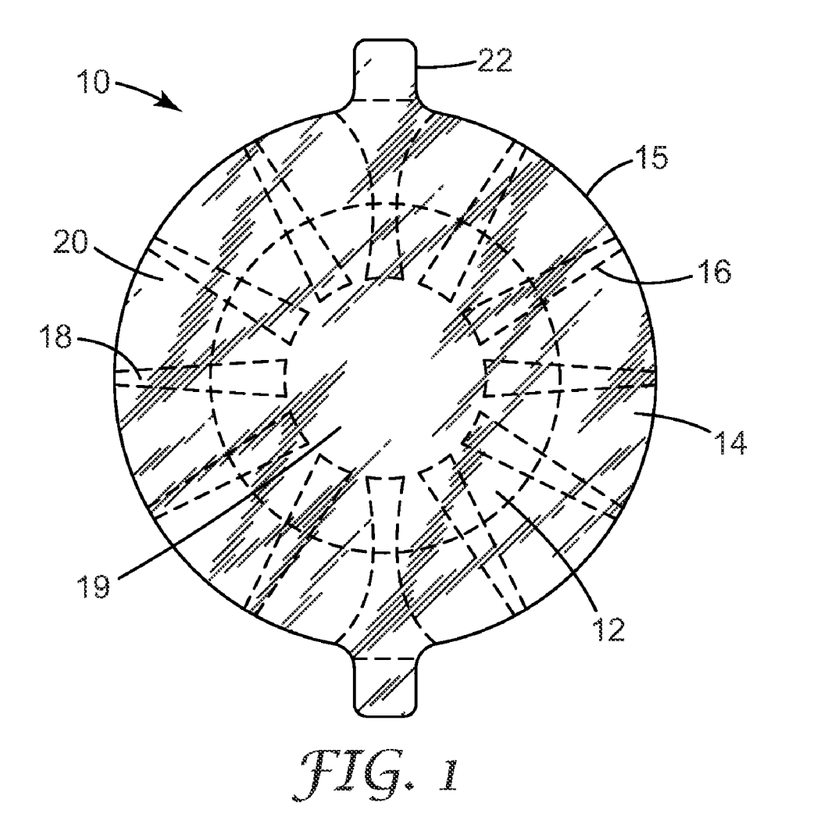
FIG. 1 is a top plan view of a wound dressing configured and arranged in accordance with one embodiment of the invention.

FIG. 1 shows one embodiment of a wound dressing and support system as described herein. The wound dressing 10 includes a centrally located absorbent pad 12. The absorbent pad 12 is covered by an adhesive layer 17 on a backing layer 14 that extends out to the perimeter 15 of the wound dressing 10. The backing layer 14 is typically extremely thin, flexible, and either transparent or translucent, allowing the absorbent pad 12 to be viewed through it. At least one dressing support layer 16 is applied to the wound dressing 10. The support system described further below is particularly useful in connection with a wound dressing 10 having a relatively heavy or stiff absorbent pad 12 positioned on a highly conformable backing layer 14 that is light and flexible relative to the pad 12.

Figure 2:
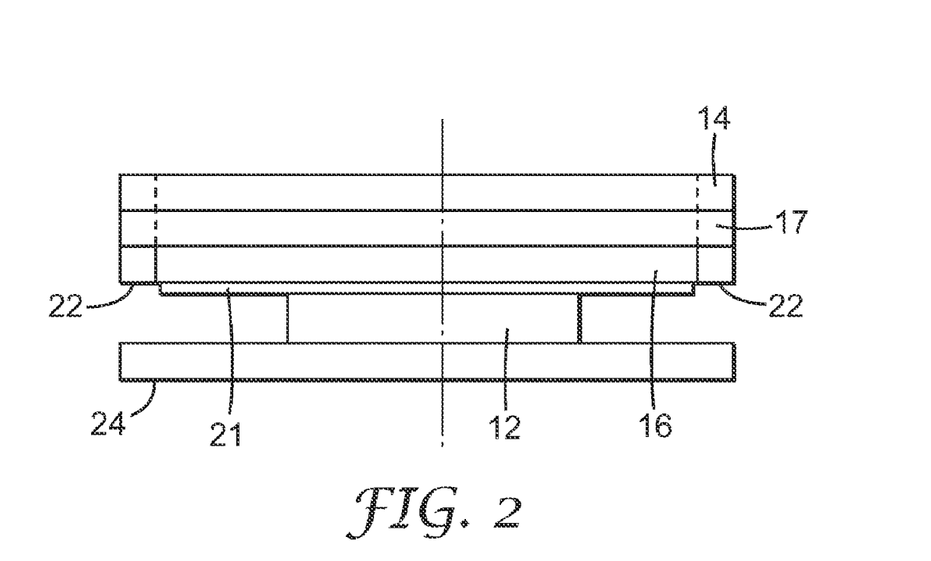
FIG. 2 is a schematic cross section of the wound dressing of FIG. 1.

FIG. 2 shows a schematic cross section of the wound dressing in FIG. 1 as viewed along the axis of an extension 18 toward the center 19 of wound dressing 10. The dressing support layer 16 is applied to the backing layer 14 on the bottom side facing the absorbent pad 12. The dressing support layer 16 can be located between the backing layer 14 and adhesive layer 17 and/or located between the adhesive layer 17 and the absorbent pad 12 (as shown in FIG. 2). In addition, the dressing support layer 16 can be applied to the top side of the backing layer 14 (on the side facing away from the absorbent pad 12) as shown in FIG. 3.

The support layer 16 in FIG. 2 also has an adhesive layer 21. This adhesive layer 21 may adhere to the patient or may facilitate attachment to the backing layer 14. The adhesive layer 21 can comprise the same materials used for adhesive 17.

Figure 3:
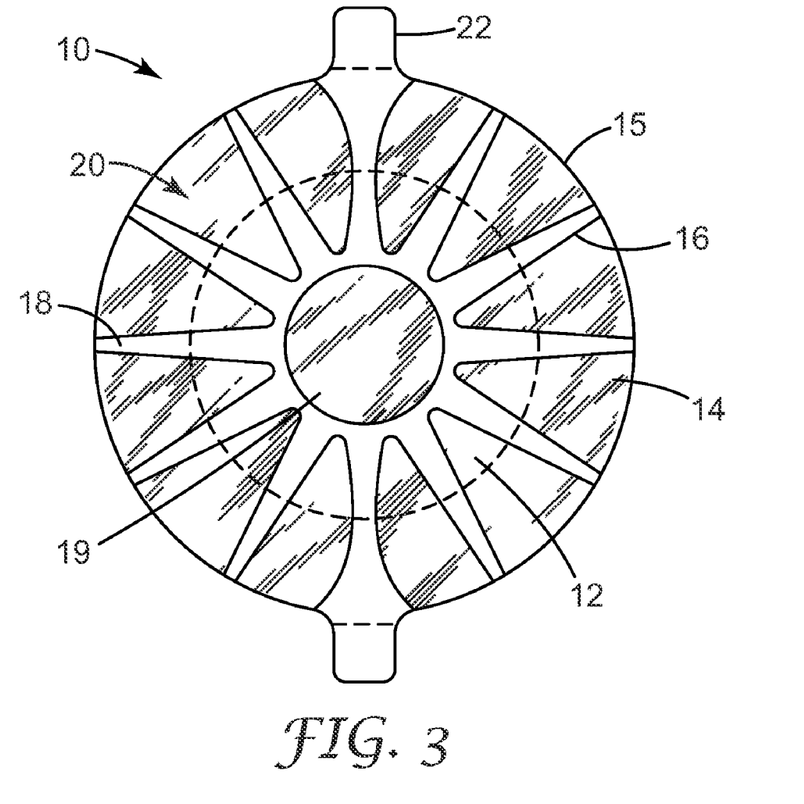
FIG. 3 is a top plan view of a wound dressing configured and arranged in accordance with one embodiment of the invention.

As shown in FIGS. 1 and 3, the dressing support layer 16 has a substantially radial configuration, with a plurality of extensions 18 radiating generally from the center 19 of the dressing 10. The support layer 16 forms a plurality of alternating uncovered portions 20 of the adhesive backing layer 14, separated from one another by the extensions 18 along the adhesive perimeter 15 of the wound dressing. The support layer 16 can be a single piece of material, such as a nonwoven material or a polymeric film, or can be two or more distinct pieces. The support layer 16 in FIG. 1 includes multiple separate pieces of nonwoven material as exemplified in Example 1. FIG. 3 shows a single piece of polymeric film provided in multiple layers, as exemplified in Example 2.

In most embodiments the support layer 16 comprises a plurality of extensions 18 radiating from the interior of the dressing 10 toward its edges. The radial configuration of the dressing support layer 16 allows the perimeter 15 of the dressing 10 to be pressed around a convex surface. During application, the uncovered portions 20 of the backing layer 14 between the extensions 18 can contract to maintain a good seal around the edges of the wound. This contraction is typically localized so that individual portions 20 will contract and even fold upon themselves. However, folds or contact between the portions 20 is minimized. In this manner, the wound dressing 10 can have a relatively even, smooth edge without major flaps of the backing layer 14 folded over onto itself.

In certain embodiments, at least some of the plurality of extensions 18 narrow as they approach the perimeter 15 of the dressing 10. The plurality of extensions 18 can also widen as they approach the perimeter 15 of the dressing 10. Also, in some embodiments the wound dressing 10 comprises at least one portion that extends beyond the edge of the wound dressing 10 to form a tab 22. The tab 22 may be formed from the dressing support layer 16; a combination of the dressing support layer 16, backing layer 14, adhesive layer 17; or some other material such as paper or polymeric film. The tab 22 can be held during positioning of the wound dressing 10.

In the embodiments shown in FIGS. 1 and 3, the extensions 18 converge on the center 19 of the wound dressing 10 but may or may not cover the center 19. In general, the dressing support layer 16 is permanently adhered to the backing layer 14, (either directly or indirectly through adhesive layer 17) and remains with the backing layer on the wound dressing 10 when a user applies the dressing.

Figure 4:
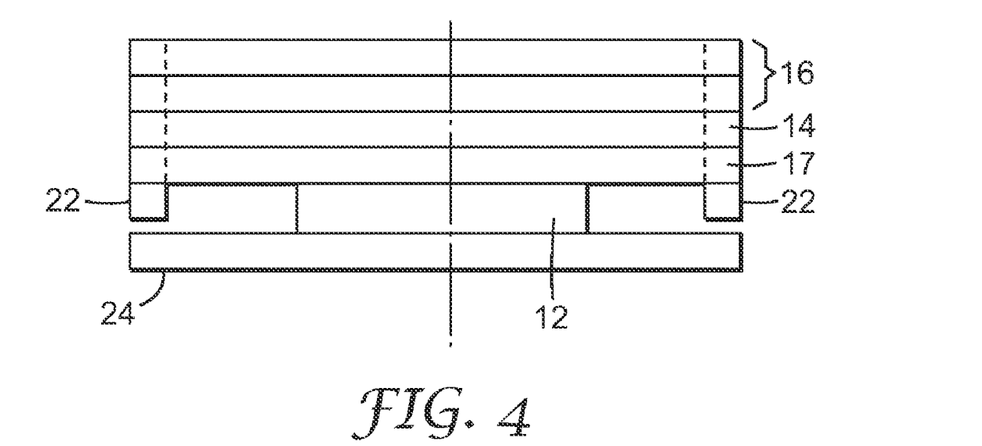
FIG. 4 is a schematic cross section of the wound dressing of FIG. 3.

As shown in FIGS. 2 and 4, the wound dressing 10 typically includes a carrier film 24, also having a tab. The carrier film 24 covers the surface of the wound dressing applied to the patient, generally making contact with the absorbent pad 12 and the periphery of the adhesive layer 17. The carrier film 24 remains attached to wound dressing 10 until a user is ready to apply the dressing. The carrier film 24 may be a single piece or multiple piece release liner, and may be part of or laminated to the package (not shown) containing the dressing, or merely enclosed along with the dressing within the package. The carrier film 24 keeps the adhesive clean during storage and shipping of the wound dressing 10. Once the carrier film 24 and dressing 10 are separated, only the support layer 16 and absorbent pad 12 provide significant rigidity to the backing layer 14.

As shown in FIGS. 1-4, the absorbent pad 12 of dressing 10 is sometimes referred to as an "island pad" because the backing layer 14 extends substantially beyond the absorbent pad 12, typically beyond the entire periphery of the absorbent pad 12. For example, the length and width of the absorbent pad can be 6 cm by 6 cm, while a backing for this pad can be 9 cm by 9 cm. The pressure sensitive adhesive layer 17 on the peripheral portion of the backing layer 14 is thus not supported or reinforced by the relatively heavy and stiff absorbent pad 12, and absent the benefits of dressing support layer 16 would be difficult to handle without folding, wrinkling or otherwise adhering to itself, rather than adhering to the skin, before and during application.

Figure 5:
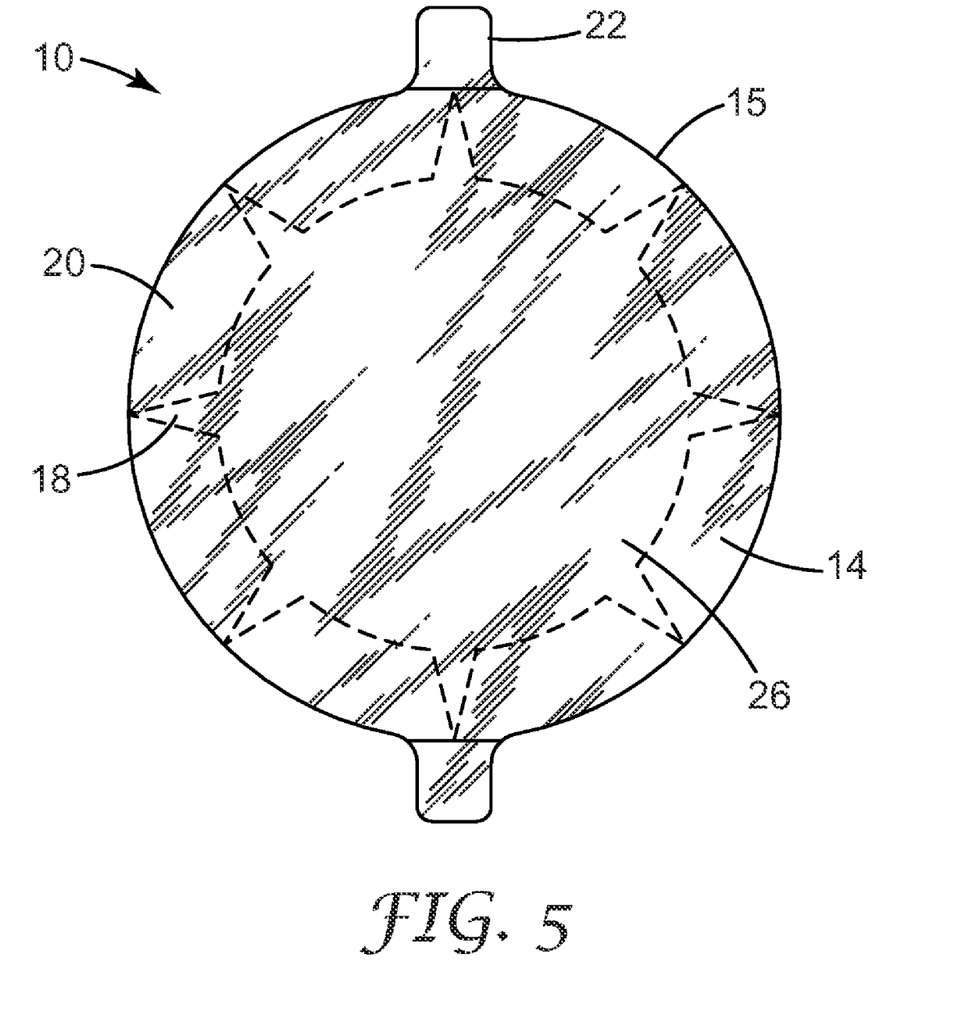
FIG. 5 is a top plan view of a wound dressing configured and arranged in accordance with an implementation of the invention.

In an alternate embodiment shown in FIG. 5, the wound dressing 10 includes a centrally located absorbent pad 26 that also functions as the dressing support layer. The absorbent pad 26 is covered by an adhesive layer 17 on a backing layer 14 that extends out to the perimeter 15 of the wound dressing 10. The backing layer 14 is typically extremely thin, flexible, and either transparent or translucent, allowing the absorbent pad 26 to be viewed through it.

In certain embodiments of the invention the absorbent pad 26 has a substantially radial configuration, with a plurality of extensions 18 radiating generally from the center 19 of the dressing 10. The absorbent pad 26 forms a plurality of alternating uncovered portions 20 of the adhesive backing layer 14, separated from one another by the extensions 18 along the adhesive perimeter 15 of the wound dressing.

In most embodiments the absorbent pad 26 comprises a plurality of extensions 18 radiating from the interior of the dressing 10 toward its edges. The radial configuration of the absorbent pad 26 allows the perimeter 15 of the dressing 10 to be pressed around a convex surface. During application, the uncovered portions 20 of the backing layer 14 between the extensions 18 can contract to maintain a good seal around the edges of the wound.

Various other implementations are appropriate in order to add or take away from the aspects shown in FIGS. 1-5. For example, the backing layer 14 can be multiple films or coatings without diverging from the invention or deviating from the meaning of the term "film" as used herein. Similarly, the absorbent pad 12 can include multiple sub-layers, including films, webs, sheets, etc. Also, additional layers and films of other materials can be added between the materials described herein without deviating from the invention.

The number of exposed areas 20 of backing layer 14 along the perimeter 15 of the wound dressing 10 can vary in number, shape, and size. However, typically there are at least four distinct exposed areas, generally at least six distinct exposed areas, generally at least eight, and more commonly twelve or more distinct areas. In some implementations less than 80 percent of the periphery (that portion outside of the absorbent) of the backing layer 14 is supported by the support layer 16 (or absorbent pad 26 as shown in FIG. 5), while in other implementations less than 60 percent of the periphery of the backing layer 14 is supported by the support layer 16 (or absorbent pad 26), while in yet other implementations less than 40 percent of the periphery of the backing layer 14 is covered by the support layer 16 (or absorbent pad 26).

The wound dressing 10 is typically applied to a patient by first cleaning the wound and making sure the area around the wound is ready to receive a dressing. The carrier film is then removed from the dressing, exposing the bottom of the absorbent pad 12 (or absorbent pad 26), the perimeter of the adhesive layer 17 and the backing layer 14. This perimeter of the backing layer 14 is maintained in a generally planar or stretched orientation by the numerous extensions 18 in the support layer 16 (or absorbent pad 26). The center of the absorbent pad 12 (or absorbent pad 26) is brought in contact with the wound, and then the edges of the dressing 10 are gently and smoothly pressed against the patient, thereby bringing the exposed adhesive perimeter of the backing layer 14 in contact with the patient. Generally the areas 20 of the backing layer 14 intermediate the extensions 18 contract to conform around the skin surface.

In certain embodiments, pressure sensitive adhesive layer 17 is provided on one major surface of the backing layer 14 in order to make it adhesive, and a low adhesion coating (low adhesion backsize or LAB) can be provided on the other major surface of the backing layer 14. The low adhesion coating reduces the need to change the dressing 10 due to unwanted dressing removal when other tapes or devices are placed on the dressing 10 and removed, and reduces the surface friction of the dressing 10 on linen or other fabrics, thereby offering additional protection against the accidental removal of dressing 10. A description of a low adhesion backing material suitable for use with the present invention can be found in U.S. Pat. Nos. 5,531,855 and 6,264,976, which are compatible with a heat seal bond described below, and are incorporated herein in their entirety.

The absorbent pad 12 or absorbent pad 26 can comprise a hydrocolloid and hydrogel pad having a thickness of at least 1 mm (e.g., most preferably 3-9 mm), and the backing layer 14 can comprise a transparent elastic polymeric film (e.g., urethane) having a thickness no greater than 0.1 mm (e.g., most preferably 0.021-0.051 mm). It will be appreciated that in this embodiment the absorbent pad 12 is much thicker, stiffer and heavier than the backing layer 14.

Additional aspects of various components of the invention will now be described in greater detail.

Absorbent Pad

The absorbent pad can be manufactured of any of a variety of materials including, but not limited to, woven or nonwoven cotton or rayon. Absorbent pad is useful for containing a number of substances, optionally including antimicrobial agents, drugs for transdermal drug delivery, chemical indicators to monitor hormones or other substances in a patient, etc.

The absorbent may include a hydrocolloid composition, including the hydrocolloid compositions described in U.S. Pat. Nos. 5,622,711 and 5,633,010, the disclosures of which are hereby incorporated by reference. The hydrocolloid absorbent may comprise, for example, a natural hydrocolloid, such as pectin, gelatin, or carboxymethylcellulose (CMC) (Aqualon Corp., Wilmington, Del.), a semi-synthetic hydrocolloid, such as cross-linked carboxymethylcellulose (X4ink CMC) (e.g. Ac-Di-Sol; FMC Corp., Philadelphia, Pa.), a synthetic hydrocolloid, such as cross-linked polyacrylic acid (PAA) (e.g., CARBOPOL™ No. 974P; B. F. Goodrich, Brecksville, Ohio), or a combination thereof. Generally, the hydrocolloid absorbent component comprises from about 5 percent to about 60 percent by weight of the absorbent composition. When preparing an absorbent composition for use in a wound dressing the hydrocolloid absorbent preferably comprises from about 20 percent to about 40 percent by weight of the composition. Absorbent materials may also be chosen from other synthetic and natural hydrophilic materials including polymer gels and foams.

Backing Materials

Suitable backing materials for the backing layer include, for example, nonwoven fibrous webs, woven fibrous webs, knits, films and other familiar backing materials. The backing materials are typically translucent or transparent polymeric elastic films. The backing can be a high moisture vapor permeable film backing. U.S. Pat. No. 3,645,835 describes methods of making such films and methods for testing their permeability.

The backing advantageously should transmit moisture vapor at a rate equal to or greater than human skin. In some embodiments, the adhesive coated backing layer transmits moisture vapor at a rate of at least 300 $g/m^2/24$ hrs/37° C./100-10% RH, frequently at least 700 $g/m^2/24$ hrs/37° C./100-10% RH, and most typically at least 2000 $g/m^2/24$ hrs/37° C./100-10% RH using the inverted cup method.

The backing layer is generally conformable to anatomical surfaces. As such, when the backing layer is applied to an anatomical surface, it conforms to the surface even when the surface is moved. The backing layer is also conformable to animal anatomical joints. When the joint is flexed and then returned to its unflexed position, the backing layer can be made such that it stretches to accommodate the flexion of the joint, but is resilient enough to continue to conform to the joint when the joint is returned to its unflexed condition.

A description of this characteristic of backing layers for use with the wound dressings described herein can be found in issued U.S. Pat. Nos. 5,088,483 and 5,160,315. Specific suitable backing materials are elastomeric polyurethane, copolyester, or polyether block amide films. These films combine the desirable properties of resiliency, high moisture vapor permeability, and transparency found in backings.

Support Layer

The material used to form the support layer is generally substantially more rigid than the backing layer to prevent the backing layer from improperly wrinkling during application to a patient. In general, the support layer materials can include, but are not limited to, an elastic film, a non-elastic film, non-woven fibrous web, woven fibrous web, knits, and polyethylene/vinyl acetate copolymer-coated papers and polyester films. FIG. 1 depicts a support layer 16 made from a nonwoven fibrous web, as described in Example 1. In FIG. 2, the support layer 16 is a multilayered elastic film, as described in Example 2.

In those embodiments in which the dressing support layer also functions as the absorbent pad, the materials listed above for the absorbent pad are also suitable for the dressing support layer. In FIG. 5, the absorbent pad 26 is a foam, as described in Example 4.

The dressing support layer is permanently adhered or attached to the backing layer either directly or by an adhesive layer. The support layer can be formed by cutting the support layer in the desired pattern, and laminating the support layer with an adhesive to the backing layer. The dressing support layer can also be laminated to the adhesive layer 17 to attach the support layer 16 to the backing layer 14 as shown in FIG. 1.

Other ways of permanently attaching the dressing support layer include irreversible heat bonding or ultrasonically welding of the dressing support layer to the backing layer. The dressing support layer can be attached on the top of the backing layer, between the backing layer and the adhesive layer, or attached to the adhesive layer.

Another method to create a rigid dressing support layer uses a curable oligomeric mixture that is applied to the backing layer in the desired pattern and then cured. The material can be thermally curable, radiation-curable, or otherwise curable as is known in the art.

As used herein, "radiation curable" refers to functionality directly or indirectly pendant from a monomer, oligomer, polymer, or surface-treated particle (as the case may be) that participate in polymerization and/or crosslinking reactions upon exposure to a suitable source of radiation. Such functionality generally includes not only groups that polymerize or crosslink via a cationic mechanism upon energy exposure, but also groups that polymerize or crosslink via a free radical mechanism.

Suitable sources of radiation include lasers, electron beams, gamma rays, mercury lamps, xenon lamps, carbon arc lamps, tungsten filament lamps, sunlight, and the like.

Representative examples of curable groups include epoxy groups, (meth)acrylate groups, olefinic carbon-carbon double bonds, allyloxy groups, alpha-methyl styrene groups, (meth)acrylamide groups, cyanate ester groups, vinyl ether groups, combinations of these, and the like. Free radically polymerizable groups are preferred. Those having (meth)

acryl moieties are most preferred. The term "(meth)acryl", as used herein, encompasses acryl and methacryl.

Materials for radiation curing can be acrylate monomers and reactive oligomers, acrylated polyurethanes or similar oligomers, vinyl-terminated oligomers of unsaturated monomers such as synthetic rubbers. Synthetic rubbers include butyl rubber, a copolymer of isobutylene with less than three percent isoprene, polyisobutylene, a homopolymer of isoprene, polybutadiene, styrene/butadiene rubber, polybutadiene, or styrene/butadiene rubber. Other materials for radiation curing can be polymers with suitable crosslinkers, such as polymers with copolymerized UV crosslinkers (as described in U.S. Pat. Nos. 4,737,559 and 4,847,137) or mixtures of polymers with crosslinkers.

Materials for thermal curing can be monomers or oligomers with complementary end groups that polymerize by condensation such as amine-ester pairs, alcohol-ester pairs, amine-acid pairs, amine-carbodiimide pairs, amine-isocyanate or alcohol-isocyanate pairs, and the like, and silane-terminated polymers or oligomers that condense by metal-catalyzed processes. Other materials for thermal curing can be polymer/latent crosslinker mixtures, including suitable polymers mixed with melamines for reaction with hydroxyl or amine functionality, silanes for hydroxyl functionality, aziridines for hydroxyl or carboxyl functionality, and the like. Other materials for thermal curing could be arrays of solid particles that are fused thermally to make a suitable support.

Yet another method of creating a dressing support layer includes coating a polymeric material on one side of the backing layer. The polymeric material can be coated by hot-melt, solvent, spray, meltblowing, pattern coating from a patterned die or from a guided nozzle or by a printing process or by other suitable means, on to the backing layer. The pattern of the dressing support layer using the polymeric material can be applied by applying pattern coated polymeric materials to a substrate onto which the backing layer is formed; by applying pattern coated polymeric material, either adhesive or non-adhesive, onto the adhesive layer, and then forming the backing layer on the adhesive layer; and by applying pattern coated polymeric material, either adhesive or non-adhesive, onto a suitable substrate onto which is then formed the adhesive layer followed by the backing layer.

Deposition can be accomplished by printing by conventional means or by ink-jet methods (as described in PCT Publication No. WO 2006/020584), by means of a suitable array of nozzles or orifices, by adhesive transfer through a mask (as described in U.S. Pat. No. 6,461,467) or by coating through a mask, by placement of a suitable tape-like strip, by forming support units in a mold and curing (as described in U.S. Patent Publication No. 2003/0194526), by photolithography, or by filling vacuum-formed cavities in the dressing film and filling with a curable composition.

Techniques for creating patterns are known, such as flexography, screen printing, spraying, and lamination of die-cut adhesives. The requirements and capabilities of each method are distinct, and have advantages and disadvantages depending on the material to be coated, the nature of the substrate onto which it is to be coated, the nature of the information to be printed, and the resolution required.

Flexographic printing and screen printing typically are used with materials with little or no crosslinking and typical viscosities in the ranges of 100 milliPascal·seconds (mPa·s) to 500 mpa·s and 2000 mPa·s to 5000 mPa·s, respectively. Die-cutting of material and subsequent lamination can been used. Noncontact printing techniques using an ink jet printer, such as ink jet imaging techniques to form printed features on a wide variety of substrates.

Pressure Sensitive Adhesive

Various pressure sensitive adhesives can be used to form an adhesive layer on the backing layer to make it adhesive. The pressure sensitive adhesive is usually reasonably skin compatible and "hypoallergenic", such as the acrylate copolymers described in U.S. Pat. No. RE 24,906. Particularly useful is a 97:3 iso-octyl acrylate: acrylamide copolymer, as is 70:15:15 isooctyl acrylate: ethyleneoxide acrylate: acrylic acid terpolymer described in U.S. Pat. No. 4,737,410. Additional useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323, 557.

Carrier Films

Carrier films suitable for use with the invention can be made of kraft papers, polyethylene, polypropylene, polyester or composites of any of these materials. The films are preferably coated with release agents such as fluorochemicals or silicones. For example, U.S. Pat. No. 4,472,480, the disclosure of which is hereby incorporated by reference, describes low surface energy perfluorochemical liners. The liners are papers, polyolefin films, or polyester films coated with silicone release materials. Examples of commercially available silicone coated release papers are POLYSLIK™, silicone release papers available from Rexam Release (Bedford Park, Ill.) and silicone release papers supplied by Loparex Group (Willowbrook, Ill.).

EXAMPLES

This invention is further illustrated by the following examples that are not intended to limit the scope of the invention. These examples are merely for illustrative purposes only and are not meant to be limiting on the scope of the appended claims.

Example 1

A laminate of the backing layer 14 and adhesive layer 17 as shown in FIGS. 1-2 was prepared from an adhesive layer comprising 70:15:15 isooctyl acrylate; ethyleneoxide acrylate: acrylic acid terpolymer made as described in U.S. Pat. No. 4,737,410 and approximately 1 mil of polyurethane film layer extruded from polyurethane resin Estane 58309 (commercially available from Noveon, Inc., Cleveland, Ohio). The laminate size was approximately 5"×6" oval shape with tabs.

The material side of approximately ten strips (each approximately ½" wide) of 3M MEDIPORE Tape with liner (commercially available from 3M Company, St. Paul, Minn.) was laminated to the adhesive side of the laminate. One end of the tape strip faced towards the center of the laminate, and the other end extended to the perimeter of the dressing, as further shown in FIG. 1. The liners from the 3M MEDIPORE Tape strips were removed after the lamination in order to expose the adhesive side of the MEDIPORE Tape. Removable tabs for handling the dressing were made by placing paper (Warm Gray 60# All purpose C1S Litho Facer Stock No. LABL-220060, commercially available from Tapemark, West St. Paul, Minn.) to the adhesive side of the laminate at the tab location only, and creating lines of separation such as a perforation at the tab location in order to facilitate removal of the tab after application.

An approximately 3"×4" oval shaped absorbent foam pad was cut from a bulk supply of the same foam that is used in 3M Tegaderm Foam Adhesive dressing (i.e., Catalog No.

90616), (commercially available from 3M Company, St. Paul, Minn.). The foam was then placed onto the adhesive side of the prototype construction described above. The resulting dressing was highly conformable yet the film edge did not fold-over onto itself, which enabled application to a body site.

Example 2

For this example, the polyurethane film and adhesive laminate from Example 1 was used with a 3M Tegasorb THIN hydrocolloid dressing (Catalog Number 90021) to make a highly conformable wound dressing as shown in FIGS. 3-4. To make the dressing, the support film layer on the top of the backing layer of a Tegasorb THIN dressing was first removed. Then, a layer of the polyurethane film and adhesive laminate from Example 1 was cut into a "spoke" pattern and carefully laminated to the top of the exposed backing layer of the Tegasorb THIN dressing. This step was then repeated to make two layers of laminate on top of the Tegasorb THIN dressing. The product release liner was then removed and the resulting dressing was highly conformable yet the film edge did not fold-over onto itself, which enabled application to a body site.

Example 3

This example was identical to Example 2 except a single layer of 2 mil polyester film with an adhesive layer (97:3 isooctylacrylate:acrylamide described in U.S. Pat. No. 4,737,410) was laminated to the top of the exposed backing layer of the 3M Tegasorb THIN hydrocolloid dressing (Catalog Number 90021). The support film layer of the hydrocolloid dressing (except for tabs) was removed prior to the lamination step. The product release liner was then removed and the resulting dressing was highly conformable yet the film edge did not fold-over onto itself, which enabled application to a body site.

Example 4

For Example 4, the absorbent pad can also be the dressing support layer, as depicted in FIG. 3. The absorbent pad could be the foam as described in Example 1 or the hydrocolloid as described in Example 2. The absorbent pad could be cut or formed in a pattern and applied to the adhesive laminate as provided in Example 1.

As various changes could be made in the above constructions, compositions and methods without departing from the scope of the invention as defined in the claims, it is intended that all matter contained in the above description or shown in the accompanying drawings be interpreted as illustrative and not in a limiting sense.

What is claimed is:

1. A wound dressing and support system comprising:
a wound dressing substrate configured to be placed on a wound, the dressing substrate having an absorbent interior surrounded by a flexible less absorbent periphery; and
a dressing support substrate configured to be permanently attached to the wound dressing substrate wherein the support substrate has one or more portions positioned proximate a center of the wound dressing and a plurality of extensions radiating from the one or more portions toward the periphery of the dressing substrate, wherein the extensions converge on the center of the wound dressing but do not cover the center of the dressing.

2. The wound dressing and support system of claim 1, wherein at least some of the plurality of extensions narrow as they approach the edge of the wound dressing substrate.

3. The wound dressing and support system of claim 1, wherein the wound dressing comprises at least two extensions beyond the edge of the wound dressing substrate to aid in positioning of the dressing.

4. The wound dressing and support system of claim 1, wherein less than 80 percent of the less absorbent periphery of the wound dressing substrate is covered by the dressing support substrate.

5. The wound dressing and support system of claim 1, wherein less than 60 percent of the less absorbent periphery of the wound dressing substrate is covered by the dressing support substrate.

6. The wound dressing and support system of claim 1, wherein the less absorbent periphery of the wound dressing comprises at least eight distinct uncovered areas.

7. The wound dressing and support system of claim 1, wherein the absorbent interior comprises a hydrocolloid absorbent sheet material.

8. The wound dressing and support system of claim 1, wherein the less absorbent periphery comprises a transparent or translucent polymeric film.

9. A wound dressing and support system comprising:
a wound dressing comprising: an elastic film backing having first and second major surfaces and a periphery; an adhesive on the first major surface of the backing; and an absorbent pad attached to the adhesive on the first major surface of the backing, wherein the absorbent pad has a size and position along the backing such that the periphery of the backing extends substantially beyond the absorbent pad, wherein the absorbent pad comprises hydrocolloid or hydrogel materials, wherein the absorbent pad is substantially thicker, heavier and stiffer than the elastic film backing; and
a support system comprising: a support layer permanently attached to the second major surface of the backing, wherein the support layer comprises a plurality of extensions radiating from a center of the wound dressing toward the outer edge of the periphery of the wound dressing, wherein the plurality of extensions converge on the center of the wound dressing but do not cover the center of the dressing and form a plurality of alternating covered and uncovered portions of the periphery of the elastic film backing, and wherein the support layer is substantially more rigid than the backing to facilitate handling of the dressing.

10. The wound dressing and support system of claim 9, wherein at least some of the plurality of extensions narrow as they approach the outer edge of the wound dressing.

11. The wound dressing and support system of claim 9, wherein the extensions are separated from adjacent extensions by an average of at least 20 degrees measured from the center of the extension at the extension's exterior edge.

12. The wound dressing support system of claim 9, wherein at least some of the plurality of extensions widen as they approach the edge of the dressing.

13. A wound dressing and support system comprising:
a wound dressing substrate configured to be placed on a wound, the dressing substrate having an absorbent interior surrounded by a flexible less absorbent periphery; and
a dressing support substrate configured to be permanently attached to the wound dressing substrate wherein the support substrate has one or more central portions positioned proximate a center of the wound dressing and a plurality of extensions radiating from the one or more central portions toward the periphery of the dressing substrate,
wherein less than 80 percent of the less absorbent periphery of the wound dressing substrate is covered by the dressing support substrate.

14. The wound dressing and support system of claim 13, wherein at least some of the plurality of extensions narrow as they approach the edge of the wound dressing substrate.

15. The wound dressing and support system of claim 13, wherein the wound dressing comprises at least two extensions beyond the edge of the wound dressing substrate to aid in positioning of the dressing.

16. The wound dressing and support system of claim 13, wherein the extensions converge on the center of the wound dressing but do not cover the center of the dressing.

17. The wound dressing and support system of claim 13, wherein less than 60 percent of the less absorbent periphery of the wound dressing substrate is covered by the dressing support substrate.

18. The wound dressing and support system of claim 13, wherein the less absorbent periphery of the wound dressing comprises at least eight distinct uncovered areas.

19. The wound dressing and support system of claim 13, wherein the absorbent interior comprises a hydrocolloid absorbent sheet material.

20. The wound dressing and support system of claim 13, wherein the less absorbent periphery comprises a transparent or translucent polymeric film.

21. The wound dressing and support system of claim 13, wherein the perimeter of the wound dressing comprises at least four distinct uncovered portions of the less absorbent periphery.

22. The wound dressing and support system of claim 13, wherein the dressing support layer comprises an absorbent material.

23. The wound dressing and support system of claim 13, wherein the dressing support layer comprises a curable material.

* * * * *